United States Patent [19]

Okumura et al.

[11] 4,372,850

[45] Feb. 8, 1983

[54] REVERSE-PHASE THIN LAYER CHROMATOGRAPHIC PLATE

[75] Inventors: Tamotsu Okumura, Mino; Tetsuro Kadono, Neyagawa, both of Japan

[73] Assignee: Shionogi & Co., Ltd., Osaka, Japan

[21] Appl. No.: 252,279

[22] Filed: Apr. 9, 1981

[30] Foreign Application Priority Data

Apr. 22, 1980 [JP] Japan .................................. 55-53814

[51] Int. Cl.³ ............................................ B01D 15/08
[52] U.S. Cl. .................................. 210/198.3; 427/387; 427/389.7
[58] Field of Search .................. 210/198.2, 198.3, 658; 427/199, 387, 389.7

[56] References Cited

U.S. PATENT DOCUMENTS 4,295,968 10/1981 Halpaap et al. ................... 210/198.3
4,298,500 11/1981 Abbott ............................. 210/198.2

*Primary Examiner*—John Adee
*Attorney, Agent, or Firm*—Birch, Stewart, Kolasch & Birch

[57] ABSTRACT

The conventional water-resistant silica or alumina plate for thin layer chromatography is converted into a reverse-phase thin layer chromatographic plate by tri-(lower alkyl)silylating the adsorbent in situ. The adsorbent layer containing the tri-(lower alkyl)silyloxy group is found to be superior to either of the known adsorbent layers containing mono- or di-(lower alkyl)silyloxy groups, or mono-(higher alkyl)silyloxy groups. Optimum conditions for performing a method for preparing the plate are also disclosed.

14 Claims, No Drawings

REVERSE-PHASE THIN LAYER CHROMATOGRAPHIC PLATE

BACKGROUND OF THE INVENTION

1. Field of the Invention

The present invention generally relates to the art of thin layer chromatography. Particularly, it is concerned with conversion of a conventional chromatographic plate into a reverse-phase chromatographic plate and a method for preparing the plates.

It is widely known that reverse-phase chromatography is useful in separating polar and/or labile compounds which are difficult to separate by a normal-phase chromatography.

In general, the art of reverse-phase chromatography is useful in separation or identification of natural substances or synthetic organic compounds such as steroid hormones, vitamins, naturally occuring or semi-synthetic antibiotics or synthetic bactericidal agents. A thin layer chromatographic plate can also be used for prefixing conditions under which conventional column chromatography or high performance liquid chromatography of the reverse phase system could be performed.

In order to properly perform reverse-phase thin layer chromatography, it is essential to intentionally reduce the chromatographic activity of the adsorbent to the limit of ascending the solvent for development. Namely, a satisfactory adsorbent activity should be maintained to an extent such that the developing solvent can naturally ascend at least 10 cm from the spotted line, because pressure cannot be exerted on the mobile phase.

2. Description of the Prior Art

An alkylsilylated adsorbent, silica gel having monomethylsilyoxy, dimethylsilyloxy, octylsilyloxy or dodecylsilyloxy group is known, and, at first sight, there seems to be no obstacle in obtaining a plate for reverse phase thin layer chromatography by forming a layer with one of these adsorbents. The actual preparative procedure is, however, not necessarily easy, and the obtained plates are not always satisfactory in many respects as will be elucidated hereinbelow in the Description of the Preferred Embodiments as comparative preparations.

In addition to this, uniform alkylsilylation of the entire surface of the metal oxide adsorbent layer for the intended purpose, while retaining its ascending tendency to an acceptable extent, is not always possible by a conventional method wherein the layer is simply contacted with an alkylsilylating agent such as alkylchlorosilane.

SUMMARY OF THE INVENTION

It is therefore a primary object of the present invention to provide a thin layer chromatographic plate used in reverse-phase chromatography.

It is another object of the present invention to provide a method for preparing a thin layer chromatographic plate adopted for use in reverse reversed-phase chromatography.

According to the present invention, there is provided a water-resistant thin layer chromatographic plate, convenient for reverse-phase chromatography, wherein 10-40% of the hydroxyl groups in the silica or alumina adsorbent are tri-(lower alkyl)silylated.

The qualification on the species of the alkylsilyl groups and on the extent of the alkylsilylation have been determined by the present inventors on the basis of the results of the experiments which will be disclosed later in the Description of the Preferred Embodiment as contrasted with the results obtained with the known adsorbents for use in the reverse-phase chromatography.

Namely, as a result of the study on the species of the alkylsilyloxy groups and on the extent of the alkylsilylation, it has been found that a tri-(lower alkyl)silyloxy group is superior to either of mono-(lower alkyl)-silyloxy, di-(lower alkyl)silyloxy and mono-(higher alkyl)silyloxy groups which are known to the art. It is most suitable if from 10 to 40 percent of the chromatographically active groups (hydroxyl group) remaining after the layer has been formed on the base plate are replaced by a tri-(lower alkyl)silyloxy groups, preferably 15 to 30% and most preferably about 23%.

The stated preferable ranges can be alternatively expressed as the content of the alkylsilylated carbon by elemental analysis of the adsorbent as 3–10%, 4–7% and 5.5%, respectively. A similar qualification that is applied to the silica gel adsorbent can also be applied to other adsorbents such as alumina and the like. Said adsorbent may further include an acid-resistant fluorescent material.

The base plate and the binding agent for supporting the chromatographic layer and for holding the adsorbent particles in the layer must of course be water-resistant and acid-resistant. The base plate can be exemplified as soda-lime glass as the most popular one but not excluding the use of any equivalent material such as polyolefins, polytetrafluoroolefins and metals of titanium in some exceptional cases.

As the binding agent, gypsum hemihydrate can be purposes for most uses but it may be modified by incorporation of sodium metacrylate or the like if binding of a particularly high degree is required. Commercially available inorganic adhesives such as Ceramabond (Nissan Chemical inductries Co., Ltd.) and Sumiceram (Sumitomo Chemical Industries Ltd.) can also be used.

If highly water-resistant and acid-resistant properties are required, a binding agent of glass powder employed in a sintered plate (disclosed in Japanese Patents Nos. 654,737 and 657,467 by the present inventors) may also be used.

In another aspect of the present invention there is provided a method for preparing the improved chromatographic plate, wherein a base plate, which has been previously been coated with a silica gel or alumina adsorbent layer in a conventional manner, is soaked in a solution containing an alkylsilylating agent such as tri-(lower alkyl)chlorosilane, O-methyl-o-trimethylsilyl-methylketone acetal or BSTFA in a concentration of 0.1–10%, under atmospheric pressure at 10°–30° C. for 10-30 minutes. It is also found that the soaking operation may more preferably be performed under a slightly reduced pressure of about 30 Torr in order to obtain a more uniform alkylsilylated layer.

The qualification on the method has also been determined on the basis of the results of the experiments which will be disclosed later.

DESCRIPTION OF THE PREFERRED EMBODIMENTS

In the following description, the present invention will be elucidated in more detail by referring to the preferred embodiments on the basis of the results of comparative experiments made in order to determine the critical qualification of the invention.

EXAMPLE 1

(1) Preparation of the plate:

In compliance with a conventional method, an aqueous mixture of silica gel (Merck: Silica Gel for Thin Layer Chromatography, H 60, 30 g) and gypsum hemihydrate (7.5 g) is applied on a base plate (20×20 cm, 2 mm in thickness) to form a thin layer of 0.6 mm thickness. The thickness of the thin layer, measured after being dried, is 0.3 mm. In preparing a fluorescent plate, a commercially available fluorescent material (Magnesium wolframate or Yttrium vanadate, activated with Europium or the like) or fluorescent crystallized glass (Zinc orthosilicate, activated with Manganese or Calcium wolframate, activated with Manganese and Lead, Japanese unexamined patent publication Sho 52-64,993) may be added to the aqueous mixture in 3 w/w % of the silica gel.

One of the thus obtained plates or a commercially available precoated plate [for instance, Merck: Silica Gel 60 (Cat. No. 5,715) and Mackery Nagel: M.N. SIL G-25 (Cat. No. 21,031)] is subjected to alkylsilylation under conditions shown below:

Silylating agent:
  (i) Methyltrichlorosilane (RP-1, Wako Chemical Co., Ltd.)
  (ii) Dimethyldichlorosilane (RP-2, Wako Chemical)
  (iii) Trimethylchlorosilane (RP-3, Wako Chemical)
  (iv) Octyltrichlorosilane (RP-8, Tokyo Kasei Co., Ltd.)
  (v) Dodecyltrichlorosilane (RP-12, Tokyo Kasei)
  (vi) Octadodecyltrichlorosilane (RP-18, Tokyo Kasei)

Solvent: Chloroform or Dichloromethane.
Concentration: 0.6, 1.25, 2.5, 5 and 10 (w/w %)

The plate is soaked in a solution of one of the listed silylating agents and maintained under slightly reduced pressure (30 mm Torr) at 25° C. for 30 minutes, then lifted and dried in a conventional manner.

The dried plate is then soaked in methanol to inactivate the unsilylated silanol residue and dried again to obtain a plate exemplified in Table 1 below.

TABLE 1

| Silylating agent. | Content of alkylsilylated carbon (%, elemental analysis). | Surface coverage by alkylsilylation. (%) |
| --- | --- | --- |
| RP-1 | 3.70–4.10 | 46.8–51.9 |
| RP-2 | 4.63–4.73 | 29.5–30.0 |
| RP-3 | 4.86–6.13 | 20.5–25.8 |
| RP-8 | 7.48–7.78 | 11.9–12.4 |
| RP-12 | 10.17 | 10.7 |
| RP-18 | 13.48–14.07 | 9.5–9.9 |

(1.25 w/w % Chloroform solution of alkylchlorosilane)

(2) Evaluation of the alkylsiloxy groups:
  (1) Separation of steroid hormones:

Separation of a sample of steroid is performed by the reverse-phase chromatography employing the six plates listed in Table 1 above, to give results summarized in Table 2, below.

TABLE 2

| | Rf value (×100) of the steroid hormones | | | | |
| --- | --- | --- | --- | --- | --- |
| | Betamethasone | | | Average separation factor* ($\bar{a}$) | Solvent front | Developing time (min./10cm) |
| Plate | (free) | (21-acetate) | (17,21-dipropionate) | | | |
| RP-1 | 71 | 65 | 50 | 1.20 | Normal | 60 |
| RP-2 | 59 | 50 | 29 | 1.45 | Normal | 60 |
| RP-3 | 57 | 48 | 27 | 1.49 | Normal | 60 |
| RP-8 | 63 | 55 | 36 | 1.34 | Irregular | 70 |
| RP-12 | 58 | 51 | 32 | 1.35 | Irregular | 100 |
| RP-18 | 54 | 48 | 31 | 1.34 | Irregular | 120 |

Developing solvent: Methanol: water (2:1, v/v) for RP-1–RP-3, Methanol: water (3:1, v/v) for RP-8–RP-18.
(Excessively large water-repelling property of RP-8–RP-18, failed in development with the former solvent system of 2:1)
*Average separation factor ($\bar{a}$): a mean value of quotient obtained by dividing high Rf value by low Rf value.

As indicated in Table 2 above, the plate RP-3 shows a maximum average separation factor to represent the best separation. With increase in the water content of the mobile phase, separation is affected and the solvent front becomes indefinite and irregular in RP-8, RP-12 and RP-18.

Another series of separation is performed on RP-1, RP-2 and RP-3 with a sample containing an additional compound (17-valerate) to give results summarized in Table 3, below.

TABLE 3

| | Rf value (×100) of the steroid hormones | | | | |
| --- | --- | --- | --- | --- | --- |
| | Betamethasone | | | | Average separation factor ($\bar{a}$) |
| Plate | (free) | (21-acetate) | (17-valerate) | (17,21-dipropionate) | |
| RP-1 | 71 | 65 | 58 | 50 | 1.12 |
| RP-2 | 68 | 57 | 45 | 36 | 1.24 |
| RP-3 | 57 | 48 | 33 | 27 | 1.29 |

Developing solvent: Methanol: water (2:1, v/v)
Detection: Fluorescene quenching and staining with sulfuric acid.

In this case again, the RP-3 plate shows a high average separation factor as compared with those of RP-1 and RP-2 plates and is found to have the maximum separation. These results, combined with those in Table 2, serve to demonstrate that the RP-3 plate is the most convenient for reverse-phase chromatography of steroid hormones.

(2) Separation of cephalosporin antibiotics:

Three selected plates (RP-2, RP-3 and RP-18) in Table 1 are used in separating a sample containing four cephalosporin antibiotics (Cefaloridine, Cefaloglycine, Cefalexin and Cefalotin) to give the results summarized in Table 4 below.

TABLE 4

| | Rf value (×100) of the cephalosporins | | |
| --- | --- | --- | --- |
| Plate | RP-2 | RP-3 | RP-18 |
| Cefaloridine | 34 | 25 | 17$^t$ |
| Cefaloglycine | 51$^t$ | 37 | 20$^t$ |
| Cefalexin | 51$^t$ | 44 | 40$^t$ |
| Cefalotin | 58 | 56 | 75 |
| Average separation factor ($\bar{a}$) | 1.21 | 1.31 | 1.69 |
| Developing rate (Min./9 cm) | 75 | 90 | 105 |

TABLE 4-continued

| | Rf value (×100) of the cephalosporins | | |
|---|---|---|---|
| Plate | RP-2 | RP-3 | RP-18 |
| Chromatogram | Fair | Good | Poor |

(ᵗindicates a tailing spot)
Developing solvent: Methanol: water (1:4, v/v) for RP-2 and RP-3, Methanol: water (1:1, v/v) for RP-18.
Detection: Fluorescene quenching method, and staining with iodine vapour and ninhydrin.

As can be seen from Table 4, the plate RP-3 is the most suitable for the separation of the tested antibiotics sample containing four cephalosporins.

In this connection, it is noteworthy that reverse-phase chromatography with organic mobile phases containing 50% of water (methanol:water=1:1) and 80% of water (methanol:water=1:4) is unable to be applied to presently commercially available plates for reverse-phase chromatography.

(3) Separation of synthetic bactericidal sulfonamides:

The three plates listed in Table 1 are used for separating a sample containing five species of sulfonamides and related compounds in the reverse-phase chromatography to give the results summarized in Table 5 below.

TABLE 5

| | Rf value (×100) of the sulfonamides | | |
|---|---|---|---|
| Plate | RP-2 | RP-3 | RP-18 |
| $N^4$—acetylsulfamethoxazole | 15 | 12 | 28ᵗ |
| Sulfamethoxazole | 25 | 24 | 49ᵗ |
| Sulfamerazine | 35 | 31 | 54 |
| Sulfadiazine | 75 | 67 | 86 |
| Sulfanilamide | 75 | 78 | 86 |
| Average separation factor ($\bar{\alpha}$) | 1.55 | 1.65 | 1.36 |
| Developing rate (Minutes/10 cm) | 95 | 95 | 90 |

(ᵗindicates tailing spot)
Developing solvent: Methanol: water (1:3) for RP-2 and RP-3
Methanol: water (1:1) for RP-18
Detection: Fluorescene quenching, and staining with Ehrlich reagent or iodine vapour.

In this case again, it is found that the plate RP-3 is the most suitable for separation as in the previous case of cephalosporin antibiotics. In particular, sulfadiazine and sulfanilamide are totally unable to be separated on either of the plates RP-2 and RP-18.

(3) Evaluation of the concentration of the alkylsilylating agent:

The effect of the change in the concentration of the alkylsilylating agent (RP-3) used in the preparation, on the separation was investigated on a series of the reverse-phase chromatography of a steroid hormone sample to give the results shown in Table 6 below. Other conditions in the preparation are similar to those described in (1) above.

TABLE 6

| | Rf value (×100) of the steroid hormones | | | | |
|---|---|---|---|---|---|
| | Concentration of trimethylchlorosilane (%, w/v) in chloroform | | | | |
| Steroid | 10 | 5 | 2.5 | 1.25 | 0.6 |
| Betamethasone | 45 | 58 | 63 | 63 | 75 |
| Betamethasone, 21-acetate | 32 | 48 | 54 | 54 | 63 |
| Betamethasone, 17-propionate | 27 | 40 | 48 | 48 | 55 |
| Betamethasone, 17,21-dipropionate | 13 | 28 | 35 | 35 | 41 |
| Average separation factor ($\bar{\alpha}$) | 1.56 | 1.28 | 1.22 | 1.22 | 1.22 |

Developing solvent: Methanol: water (2:1, v/v)
Detection: Fluorescence quenching and staining with sulfuric acid.

From Table 6, it is recognized that the higher the concentration of the alkylsilylating agent the higher the average separation factor will be, but the smaller the Rf value will become, and that the small Rf values are stable in a concentration range of 0.6–2.5%, w/v. The surface coverage by this alkylsilylation is in a range of approximately 20–26%.

Namely, a concentration of the alkylsilylating agent in a range of 0.6–2.5% is sufficient for performing the alkylsilylation and one approximately 1.25% is the most suitable for the purpose in general.

EXAMPLE 2

(Preparation of plate with a glass binder):

In compliance with the method disclosed in U.S. Pat. Nos. 654,737 and 657,467 corresponding to U.S. Pat. No. 3,677,410, an acetone slurry containing either one of silica gel (Merck: Silica Gel H 60, 1 g) or alumina (Merck: Aluminum oxide T, 1 g), glass powder (soda-lime glass powder of 10 μm mean particle size, 3 g) and fluorescent material (Magnesium wolframate, 0.4 g) is applied on a glass plate (20×20 cm, thickness, 2 mm) to form a thin-layer of 0.5 mm in thickness dried, and then sintered at, 690° C. for 8 minutes. The thicknesses of the sintered layers are about 0.2 mm in both the silica gel and alumina plates.

The thus obtained plates are subjected to alkylsilylation in a manner similar to that described in Example 1 (1) to give plates for use in the reverse-phase chromatography.

Of these, trimethylsilylated plate (Rf-3) is used in separating a steroid hormone sample to give the results shown in Table 7 below.

TABLE 7

| | Rf values (×100) | |
|---|---|---|
| Steroid | (silica gel) | (alumina) |
| Betamethasone | 77 | 91 |
| Betamethasone, 21-acetate | 70 | 90 |
| Betamethasone, 17-valerate | 52 | 71 |
| Betamethasone, 17,21-dipropionate | 41 | 43ᵗ |
| Average separation factor ($\bar{\alpha}$) | 1.24 | 1.31 |
| Developing rate (minutes/10 cm) | 80 | 90 |

Developing solvent: Methanol: water (2:1, v/v) (1:1, v/v)

We claim:

1. A water-resistant thin layer chromatographic plate for reverse-phase thin layer chromatography, comprising: a base plate and a silica or alumina adsorbent wherein 10–40% of the hydroxyl groups of said adsorbent are tri-(lower alkyl)silylated.

2. The chromatographic plate according to claim 1, wherein 15–30% of said hydroxyl groups are tri(lower alkyl)-silylated.

3. The chromatographic plate according to claim 1, wherein approximately 23% of said hydroxyl groups are tri(lower alkyl)silylated.

4. The chromatographic plate according to claim 1, wherein said hydroxyl groups are trimethylsilylated.

5. The chromatographic plate according to claim 1 or 4, which further includes an acid-resistant fluorescent material.

6. A water-resistant thin layer chromatographic plate for reverse-phase thin layer chromatography, consisting essentially of: a base plate and a silica or alumina adsorbent wherein 10-40% of the hydroxyl groups of said adsorbent are tri-(lower alkyl)silylated.

7. The chromatographic plate according to claim 6, wherein said hydroxyl groups are trimethylsilylated.

8. A method for preparing a water-resistant reverse-phase thin layer chromatographic plate, comprising the steps of:

contacting a silica or alumina adsorbent which has been previously coated on a base plate with a tri-(lower alkyl)-silylating agent under conditions sufficient to replace 10-40% of the hydroxyl groups of said adsorbent with tri-(lower alkyl)-silyloxy groups.

9. The method according to claim 8, wherein 15-30% of said hydroxyl groups are replaced by tri-(lower alkyl)-silyloxy groups.

10. The method according to claim 8, wherein approximately 23% of said hydroxyl groups are replaced by tri-(lower alkyl)silyloxy groups.

11. The method according to claim 8, wherein said base plate is soaked in a 0.1 to 10 w/v% solution of an alkylsilylating agent in an organic solvent under atmospheric pressure at 10°-30° C. for 10-60 minutes.

12. The method according to claim 8, wherein said base plate is soaked in a 0.1 to 10 w/v% solution of an alkylsilylating agent in an organic solvent under a pressure of about 30 Torr at 10°-30° C. for 10-60 minutes.

13. The method according to claim 8, wherein said tri-(lower alkyl)silylating agent is a tri-(lower alkyl)-chlorosilane.

14. The method according to claim 8, wherein said tri-(lower alkyl)silylating agent is trimethylchlorosilane.

* * * * *